United States Patent
Tsubokawa et al.

(10) Patent No.: US 10,603,271 B2
(45) Date of Patent: Mar. 31, 2020

(54) ORAL COMPOSITION

(71) Applicant: NIPPON ZETTOC CO., LTD., Tokyo (JP)

(72) Inventors: Satomi Tsubokawa, Tokyo (JP); Mizuki Inagaki, Tokyo (JP)

(73) Assignee: Nippon Zettoc Co., Ltd., Tokyo (JP)

( * ) Notice: Subject to any disclaimer, the term of this patent is extended or adjusted under 35 U.S.C. 154(b) by 0 days.

(21) Appl. No.: 15/570,728

(22) PCT Filed: Oct. 7, 2016

(86) PCT No.: PCT/JP2016/080001
§ 371 (c)(1),
(2) Date: Oct. 30, 2017

(87) PCT Pub. No.: WO2017/199453
PCT Pub. Date: Nov. 23, 2017

(65) Prior Publication Data
US 2019/0060214 A1      Feb. 28, 2019

(30) Foreign Application Priority Data

May 18, 2016  (JP) ................................ 2016-099260

(51) Int. Cl.
| A61K 8/9789 | (2017.01) |
| A61Q 11/00 | (2006.01) |
| A61K 36/346 | (2006.01) |
| A61K 8/97 | (2017.01) |
| A61K 36/804 | (2006.01) |
| A61K 36/539 | (2006.01) |
| A61Q 11/02 | (2006.01) |

(52) U.S. Cl.
CPC .............. *A61K 8/9789* (2017.08); *A61K 8/97* (2013.01); *A61K 36/346* (2013.01); *A61K 36/539* (2013.01); *A61K 36/804* (2013.01); *A61Q 11/00* (2013.01); *A61Q 11/02* (2013.01)

(58) Field of Classification Search
None
See application file for complete search history.

(56) References Cited

FOREIGN PATENT DOCUMENTS

| CN | 101618155 A | 1/2010 |
| CN | 102091252 A | 6/2011 |
| CN | 102727737 A | 10/2012 |
| CN | 102805830 A | 12/2012 |
| CN | 103656127 A | 3/2014 |
| CN | 102961318 | * 12/2014 |
| CN | 102961318 A | * 12/2014 |
| CN | 104383364 A | 3/2015 |
| CN | 104815210 A | 8/2015 |
| CN | 105434309 | * 12/2015 |
| CN | 105434309 A | * 12/2015 |
| CN | 105267777 A | 1/2016 |
| CN | 105434309 A | 3/2016 |
| CN | 105434952 A | 3/2016 |
| JP | H0625000 A | 2/1994 |
| JP | H11279039 A | 10/1999 |
| JP | 2006342069 A | 12/2006 |
| JP | 2011256136 A | 12/2011 |
| JP | 2014034552 A | 2/2014 |
| JP | 2015054847 A | 3/2015 |
| KR | 20110000241 A | 1/2011 |
| WO | 2011077983 A1 | 6/2011 |

OTHER PUBLICATIONS

Yinghong et al (Asian Journal of Chemistry, 19(2), 2007, 867-882). (Year: 2007).*
Zhao et al (Sci. Bull, 2016); (Year: 2016).*
Nyakudya et al (Prev. Nutr. Food Sci., 2014, 19(2), 59-68) (Year: 2014).*
Di Huang et al (PFAF Plant Database; https://pfaf.org/user/Plant.aspx?LatinName=Rehmannia+glutinosa, (Year: 1996).*
Takeya, K., "Antimicrobial and anti-inflammatory activities of crude drugs," Fragrance Journal , vol. 23, No. 8, Available as Early as Jan. 1, 1995, 11 pages. (Submitted with Partial Translation).
Wang, J., "Fourth Chinese medicine for oral disease," vol. 31, No. 2, Available as Early as Jan. 1, 2012, 16 pages. (Submitted with Partial Translation).

* cited by examiner

*Primary Examiner* — Celeste A Roney
(74) *Attorney, Agent, or Firm* — McCoy Russell LLP

(57) ABSTRACT

The present invention wherein an oral composition contains *Scutellaria* root and *Platycodon* root. It is preferred that the oral composition further contains *Rehmannia* root. In the oral composition, when a content ratio of the *Scutellaria* root is defined as $X_A$ [mass %] and a content ratio of the *Platycodon* root is defined as $X_B$ [mass %], it is preferred that the following relation is satisfied: $0.00005 \leq X_B/X_A \leq 20000$.

5 Claims, No Drawings

ORAL COMPOSITION

CROSS-REFERENCE TO RELATED APPLICATIONS

The present application is a U.S. National Phase of International Patent Application Serial No. PCT/JP2016/080001, entitled "ORAL COMPOSITION," filed on Oct. 7, 2016. International Patent Application Serial No. PCT/JP2016/080001 claims priority to Japanese Patent Application No. 2016-099260, filed on May 18, 2016. The entire contents of each of the above-cited applications are hereby incorporated by reference in their entirety for all purposes.

TECHNICAL FIELD

The present invention relates to an oral composition.

RELATED ART

As an oral composition, there are various kinds of oral compositions. Such oral compositions include an oral composition for physically removing plaque which adhered to teeth simply and an oral composition in which any medicinal properties are contained for expectation of various kinds of medicinal effects.

Especially, has been known an oral composition which contains a plant constituent (particularly, a crude drug having long history) derived from a natural product (see Patent Documents 1 and 2).

Further, an inhibitor containing a plant constituent has been also known as a biofilm inhibitor used for a food application and the like (see Patent Document 3).

However, recent years, it is required for such oral compositions to further improve a forming suppression effect of plaque to cause periodontal disease.

The Patent Document 1 is JP-A 2015-54847, the Patent Document 2 is JP-A H06-25000 and the Patent Document 3 is JP-A 2014-34552, which are examples of related art.

SUMMARY OF THE INVENTION

It is an object of the present invention to provide an oral composition that contains a plurality of crude drugs, has effects in a lower dosage than a use dosage of a single crude drug and has the forming suppression effect of the plaque to cause the periodontal disease.

Such an object is achieved by the present inventions (1) to (7) described below.

(1) An oral composition comprising *Scutellaria* root and *Platycodon* root.

(2) In the oral composition in the above-mentioned item (1), it is preferred that the oral composition further comprises *Rehmannia* root.

(3) In the oral composition in the above-mentioned item (2), it is also preferred that when a content ratio of the *Scutellaria* root in the oral composition is defined as $X_A$ [mass %] and a content ratio of the *Rehmannia* root in the oral composition is defined as $X_C$ [mass %], the following relation is satisfied: $0.0005 \leq X_C/X_A \leq 20000$.

(4) In the oral composition in the above-mentioned item (2) or (3), it is also preferred that when a content ratio of the *Platycodon* root in the oral composition is defined as $X_B$ [mass %] and a content ratio of the *Rehmannia* root in the oral composition is defined as $X_C$ [mass %], the following relation is satisfied: $0.0005 \leq X_C/X_B \leq 20000$.

(5) In the oral composition in any one of the above-mentioned items (1) to (4), it is also preferred that when a content ratio of the *Scutellaria* root in the oral composition is defined as $X_A$ [mass %] and a content ratio of the *Platycodon* root in the oral composition is defined as $X_B$ [mass %], the following relation is satisfied: $0.00005 \leq X_B/X_A \leq 20000$.

(6) In the oral composition in any one of the above-mentioned items (2) to (4), it is also preferred that the *Rehmannia* root is contained as an extract.

(7) In the oral composition in any one of the above-mentioned items (1) to (6), it is also preferred that at least one of the *Scutellaria* root and the *Platycodon* root is contained as an extract.

According to the present invention, it is possible to provide an oral composition that contains a plurality of crude drugs, has effects in a lower dosage than a use dosage of a single crude drug and has a forming suppression effect of plaque to cause periodontal disease.

DETAILED DESCRIPTION OF THE PREFERRED EMBODIMENTS

Hereinbelow, description will be made on preferred embodiments according to the present invention in detail.

<<Oral Composition>>

As an oral composition, there are various kinds of oral compositions. Such oral compositions include an oral composition for physically removing plaque which adhered to teeth simply and an oral composition in which any medicinal properties are contained for expectation of various kinds of medicinal effects.

Especially, there are references which disclose an oral composition containing a plant constituent (particularly, a crude drug having long history) derived from a natural product.

However, recent years, it is required to further improve a forming suppression effect of plaque to cause periodontal disease.

Therefore, the present inventors have studied hard and developed an oral composition which uses a combination of *Scutellaria* root and *Platycodon* root among various kinds of crude drugs. By using them, the present inventors have found that they act synergistically, so that it is possible to obtain excellent effects.

In other words, the oral composition of the present invention contains the *Scutellaria* root and the *Platycodon* root. By containing both of them, it is possible to obtain excellent forming suppression effect with respect to the plaque to cause the periodontal disease. Particularly, in the case where a single crude drug constituent is used, even if a content ratio thereof is low so that the effects are not obtained at all, it is possible to obtain the sufficiently excellent forming suppression effect with respect to the plaque to cause the periodontal disease.¥

In this regard, it is to be noted although the references described above disclose the various kinds of crude drugs, the references fail to disclose the oral composition using the combination of the *Scutellaria* root and the *Platycodon* root specifically.

In this present invention, the oral composition may contain the *Scutellaria* root and the *Platycodon* root, for example, in a state of having ground plants in a dry state. Further, the oral composition may contain them as extract essence extracted by using an extract solvent such as water and an organic solvent or an extract medium such as a supercritical fluid, or a constituent obtained by removing the extract medium from the extract essence (hereinafter, these are also collectively referred to as "extract").

In particular, it is preferred that the oral composition contains at least one of the *Scutellaria* root and the *Platycodon* root as the extract. It is more preferred that it contains both of the *Scutellaria* root and the *Platycodon* root as the extract.

This makes it possible to suppress variation in quality between production lots, thereby obtaining stable quality.

Further, it is possible to contain a desirable constituent among constituents derived from the natural product in a relatively high content ratio, thereby enabling a content ratio of undesirable constituents to be suppressed in low. As a result, for example, it is possible to reliably exert expected effects while preventing color tone, flavor and the like of the oral composition from being lowered. Moreover, it is possible to obtain excellent stability of an active constituent in the oral composition. Therefore, it is possible to improve preservation stability as a whole of the oral composition and prolong an expiration date of the oral composition more, so that it is possible to assist a mild condition for preservation.

Examples of the extract solvent to obtain the extracts of the *Scutellaria* root and the *Platycodon* root include: various kinds of inorganic solvents and various kinds of organic solvents. Specifically, examples of the extract solvent include: water; a monoalcohol such as methanol, ethanol, propyl alcohol, isopropyl alcohol, butanol, isobutanol, octanol, phenol and the like; a polyalcohol such as propylene glycol, 1,3-butylene glycol, 1,2-butylene glycol, 1,4-butylene glycol, 1,5-pentane diol, 1,2-pentane diol, 1,3-pentane diol, 1,4-pentane diol, 1,3,5-pentane triol, glycerin, polyethylene glycol (molecular weight of 100 to 100,000) and the like; ketones such as acetone, methyl ethyl ketone and the like; esters such as ethyl acetate, methyl acetate and the like; ethers such as diethyl ether, dimethyl ether, ethyl methyl ether, dioxane and the like; nitriles such as acetonitrile and the like; a halogenide such as chloroform, carbon tetrachloride and the like; an aliphatic hydrocarbon such as hexane, octane, cyclohexane and the like; an aromatic hydrocarbon such as xylene, toluene, benzene and the like. These materials may be used singly or in combination of two or more of them. Further, an acid in which normality has been prepared (for example, hydrochloric acid, sulfuric acid, nitric acid, phosphoric acid, formic acid and acetic acid) or an alkali (for example, sodium hydroxide, potassium hydroxide, calcium hydroxide and ammonia) may be used as the extract solvent arbitrarily.

Among them, it is preferred that an ethanol aqueous solution is used as the extract solvent to obtain the extract of the *Scutellaria* root.

In this way, the effects as described above are exerted conspicuously.

Particularly, a concentration (content ratio of the ethanol) of the ethanol aqueous solution of the extract solvent to obtain the extract of the *Scutellaria* root is preferably 30 vol % or more and 95 vol % or less and more preferably 40 vol % or more and 70 vol % or less.

In this way, the effects as described above are exerted conspicuously.

Further, it is preferred that a solvent containing water is used as the extract solvent to obtain the extract of the *Platycodon* root.

In this way, the effects as described above are exerted conspicuously.

Particularly, a content ratio of the water contained in the extract solvent to obtain the extract of the *Platycodon* root is preferably 90 vol % or more and more preferably 95 vol % or more.

In this way, the effects as described above are exerted conspicuously.

In the oral composition, the *Scutellaria* root and the *Platycodon* root may be contained in any form. For example, they may be contained in a powder manner or a particle manner, as an oil constituent, or in a state of dissolving with other constituents.

A content ratio of the *Scutellaria* root in the oral composition (content ratio of the *Scutellaria* root in the dry state) is not particularly limited, but preferably 0.0001 mass % or more and 2 mass % or less, more preferably 0.0005 mass % or more and 0.5 mass % or less, and even more preferably 0.005 mass % or more and 0.05 mass % or less.

If the content ratio of the *Scutellaria* root is smaller than the lower limit value noted above, there is a possibility that the effects of the present invention are not exerted sufficiently by depending on the content ratio of the *Platycodon* root.

On the other hand, if the content ratio of the *Scutellaria* root exceeds the upper limit value noted above, there is a case that a problem of coloring and a problem of a low sense of use by uncomfortable flavors such as bitter flavor occur more conspicuously.

A content ratio of the *Platycodon* root in the oral composition (content ratio of the *Platycodon* root in the dry state) is not particularly limited, but preferably 0.0001 mass % or more and 2 mass % or less, more preferably 0.001 mass % or more and 1 mass % or less, and even more preferably 0.025 mass % or more and 0.5 mass % or less.

If the content ratio of the *Platycodon* root is smaller than the lower limit value noted above, there is a possibility that the effects of the present invention are not exerted sufficiently by depending on the content ratio of the *Scutellaria* root.

On the other hand, if the content ratio of the *Platycodon* root exceeds the upper limit value noted above, there is a case that a problem of coloring and a problem of a low sense of use by uncomfortable flavors such as bitter flavor occur more conspicuously.

When the content ratio of the *Scutellaria* root in the oral composition is defined as $X_A$ [mass %] and the content ratio of the *Platycodon* root in the oral composition is defined as $X_B$ [mass %], the following relation is satisfied: preferably $0.00005 \leq X_B/X_A \leq 20000$, more preferably $0.002 \leq X_B/X_A \leq 2000$, and even more preferably $0.5 \leq X_B/X_A \leq 100$.

This makes it possible to obtain more excellent forming suppression effect of the plaque to cause the periodontal disease as well as the more excellent preservation stability of the oral composition.

It is preferred that the oral composition of the present invention further contains *Rehmannia* root in addition to the *Scutellaria* root and the *Platycodon* root.

As described above, by using the *Rehmannia* root, of which forming suppression effect of the plaque to cause the periodontal disease is not known in the use by itself, in the combination of the *Scutellaria* root and the *Platycodon* root, they act synergistically, so that it is possible to obtain further excellent forming suppression effect of the plaque to cause the periodontal disease. Particularly, even if the *Rehmannia* root having the concentration which does not show the effects at all by itself is added to the oral composition, it is possible to obtain the excellent forming suppression effect of the plaque to cause the periodontal disease by using it in the combination of the *Scutellaria* root and the *Platycodon* root.

In the case where the oral composition contains the *Rehmannia* root, the oral composition may contain the *Rehmannia* root, for example, in a state of having ground plants in a dry state. Further, the oral composition may contain it as extract essence extracted from the plants by using an extract solvent such as water and an organic solvent or an extract medium such as a supercritical fluid, or a constituent (extract) obtained by removing the extract medium from the extract essence.

In particular, it is preferred that the oral composition contains the *Rehmannia* root as the extract.

This makes it possible to suppress variation in quality between production lots, thereby enabling stable quality to be obtained.

Further, in the oral composition, it is possible to contain a desirable constituent contained in the *Rehmannia* root as the natural product in a relatively high content ratio, thereby enabling a content ratio of undesirable constituents to be suppressed in low. As a result, for example, it is possible to reliably exert the expected effects while preventing the color tone, the flavor and the like of the oral composition from being lowered. Moreover, it is possible to obtain further excellent stability of the active constituent in the oral composition. Therefore, it is possible to improve the preservation stability as a whole of the oral composition and prolong the expiration date of the oral composition more, so that it is possible to assist the mild condition for preservation.

Examples of the extract solvent to obtain the extract of the *Rehmannia* root include the solvents described as the extract solvent to obtain the extracts of the *Scutellaria* root and the *Platycodon* root.

Among them, it is preferred that an ethanol aqueous solution is used as the extract solvent to obtain the extract of the *Rehmannia* root.

In this way, the effects as described above are exerted conspicuously.

Particularly, a concentration (content ratio of the ethanol) of the ethanol aqueous solution of the extract solvent to obtain the extract of the *Rehmannia* root is preferably 30 vol % or more and 95 vol % or less, and more preferably 40 vol % or more and 70 vol % or less.

In this way, the effects as described above are exerted conspicuously.

In the oral composition, the *Rehmannia* root may be contained in any form. For example, it may be contained in a powder manner or particle manner, as an oil constituent, or in a state of dissolving with other constituents.

A content ratio of the *Rehmannia* root in the oral composition (content ratio of the *Rehmannia* root in the dry state) is not particularly limited, but preferably 0.001 mass % or more and 2 mass % or less, more preferably 0.05 mass % or more and 1 mass % or less, and even more preferably 0.2 mass % or more and 0.6 mass % or less.

If the content ratio of the *Rehmannia* root is smaller than the lower limit value noted above, there is a possibility that the effects due to the inclusion of the *Rehmannia* root are not exerted sufficiently.

On the other hand, if the content ratio of the *Rehmannia* root exceeds the upper limit value noted above, there is a case that a problem of coloring and a problem of a low sense of use by uncomfortable flavors such as bitter flavor occur more conspicuously.

When the content ratio of the *Scutellaria* root in the oral composition is defined as $X_A$ [mass %] and the content ratio of the *Rehmannia* root in the oral composition is defined as $X_C$ [mass %], the following relation is satisfied: preferably $0.0005 \leq X_C/X_A \leq 20000$, more preferably $0.1 \leq X_C/X_A \leq 2000$, and even more preferably $4 \leq X_C/X_A \leq 120$.

This makes it possible to obtain more excellent forming suppression effect of the plaque to cause the periodontal disease as well as the more excellent preservation stability of the oral composition.

When the content ratio of the *Platycodon* root in the oral composition is defined as $X_B$ [mass %] and the content ratio of the *Rehmannia* root in the oral composition is defined as $X_C$ [mass %], the following relation is satisfied: preferably $0.0005 \leq X_C/X_B \leq 20000$, more preferably $0.05 X_C/X_B \leq 1000$, and even more preferably $0.4 \leq X_C/X_B \leq 24$.

This makes it possible to obtain the more excellent forming suppression effect of the plaque to cause the periodontal disease as well as the more excellent preservation stability of the oral composition.

The oral composition of the present invention may contain any constituents other than the constituents described above.

Examples of such constituents (other constituents) include an abrading agent, a wetting agent, a solvent, a binder, a flavor, a diluting agent, a sweeting agent, a pH adjuster, an antiseptic agent, an emulsifying agent, a solubilizing agent, a foaming agent, a lubricant, an oil, a surfactant, a coloring agent, an antioxidizing agent, a chelate agent, a flavoring substance, a moisturizing agent, an antibacterial agent, an anti-inflammatory drug, fluoride, a vitamin preparation, crude drugs other than the crude drugs described above, and the like.

Examples of the abrading agent include: a silica-based abrading agent such as silica gel, silica having sedimentation property, silica having pyrogenic property, hydrated silicate, anhydrous silicic acid, aluminosilicate, zirconosilicate, and the like; calcium hydrogen phosphate for brushing such as dicalcium phosphate dehydrate, dicalcium phosphate nonhydrate, and the like; calcium carbonate such as light calcium carbonate, heavy calcium carbonate, and the like; calcium phosphate, trimagnesium phosphate, tricalcium phosphate, insolubility calcium metaphosphate, calcium pyrophosphate, aluminum hydroxide, aluminum oxide, magnesium carbonate, zirconium silicate, titanium dioxide, a synthetic resin-based abrading agent, zeolite, and the like. These materials may be used singly or in combination of two or more of them.

Particularly, it is preferred that the oral composition contains the abrading agent constituted of a porous body.

This makes it possible to support the crude drug constituents described above (in particular, the extract of the *Scutellaria* root and the extract of the *Platycodon* root) into pores of the abrading agent (porous body), thereby enabling the bitter flavor of the crude drugs to be reduced.

Among the abrading agents described above, it is preferred that zeolite is used particularly.

The use of zeolite is makes it possible to reliably support the crude drug constituents (in particular, the extract of the *Scutellaria* root and the extract of the *Platycodon* root) into the pores of the abrading agent (porous body), thereby enabling the bitter flavor of the crude drugs to be reduced.

Examples of the wetting agent include: a polyalcohol such as glycerin, sorbitol, polyethylene glycol, propylene glycol, ethylene glycol, 1,3-butylene glycol, polypropylene glycol, xylitol, maltitol, and lactitol; and the like. These materials may be used singly or in combination of two or more of them.

An organic solvent such as an alcohol and water are preferable as the solvent. Examples of the organic solvent include: ethanol, propylalcohol, isopropylalcohol and the like. Especially, the ethanol is preferable.

Examples of the binder include: a cellulose derivative such as carrageenan, carboxymethyl cellulose, carboxymethyl cellulose sodium and the like; alkali metal alginate such as sodium alginate and the like; gums such as xanthane gum, tragacanth gum, arabic gum and the like; a synthetic binder such as polyvinyl alcohol, sodium polyacrylate and the like; and the like. These materials may be used singly or in combination of two or more of them.

Examples of the flavor include: a flavor ingredient such as 1-menthol, 1-carvone, cinnamic aldehyde, orange oil, anethole, 1,8-cineol, methyl salicylate, eugenol, thymol, linalool, limonene, menton, methyl acetate, citral, camphor, borneol, pinene, spilanthol, ethyl acetate, ethyl butyrate, isoamyl acetate, hexanal, methyl anthranilate, ethyl methyl phenyl glycidate, benzaldehyde, vanillin, ethyl vanillin, furaneol, maltol, ethyl maltol, γ/δ-decalactone, γ/δ-undecalactone, N-ethyl-p-menthane-3-carboxamide, menthyl lactate, ethyleneglycol-1-menthyl carbonate and the like; a natural essential oil such as peppermint oil, spearmint oil, eucalyptus oil, clove oil, thyme oil, sage oil, cardamom oil, rosemary oil, marjoram oil, lemon oil, nutmeg oil, lavender oil, para cress oil and the like; a compound flavor such as apple, banana, strawberry, blueberry, melon, peach, pineapple, grape, mascat, wine, cherry, squash, coffee, brandy, yogurt and the like; which are known as flavor materials. These materials may be used singly or in combination of two or more of them.

Examples of the diluting agent include: sucrose, lactose, starch, glucose, crystalline cellulose, mannit, sorbit, xylitol, erythritol, palatinit, palatinose, maltitol, trehalose, lactitol, lactulose, hydrogenated starch hydrolysates, hydrogenated isomaltooligo saccharide, coupling sugar, gum base, arabic gum, gelatin, cethyl methyl cellulose, light anhydrous silicic acid, magnesium aluminate, calcium metasilicate aluminate, sodium hydrogen carbonate, calcium phosphate and the like. These materials may be used singly or in combination of two or more of them.

Examples of the sweeting agent include palatinit, aspartame, saccharin sodium, acesulfame potassium, stevioside, neohesperidin dihydrochalcone, glycyrrhizin, perillamin, thaumatin, aspartyl phenyl alanyl methyl ester, ρ-methoxy cinnamic aldehyde, and the like. These materials may be used singly or in combination of two or more of them.

Examples of the pH adjuster include citric acid, phosphoric acid, pantothenic acid, malic acid, pyrophosphoric acid, lactic acid, tartaric acid, glycerophosphoric acid, acetic acid, nitric acid, a chemically possible salt such as disodium hydrogenphosphate, sodium hydroxide, and the like. These materials may be used singly or in combination of two or more of them so that the pH of the composition falls within a suitable range.

Examples of the antiseptic agent include para-hydroxy benzonates, benzoic acid and a salt thereof, salicylic acid and a salt thereof, sorbic acid and a salt thereof, phenoxyethanol, alkyldiamino ethylglycine hydrochloride, and the like. These materials may be used singly or in combination of two or more of them.

Examples of the emulsifying agent include polyoxyethylene alkyl ether, polyoxyethylene fatty acid ester, polyoxyethylene sorbitan fatty acid ester, sorbitan fatty acid ester, glycerine fatty acid ester, polyglycerine fatty acid ester, polyoxyethyele hydrogenated castor oil, sodium stearoyl lactate, soy phospholipid, chloride alkyl trimethyl ammonium, and the like. These materials may be used singly or in combination of two or more of them.

Examples of the solubilizing agent include esters, polyethylene glycol derivatives, polyoxyethylene hydrogenated castor oil, sorbitan fatty acid esters, sulfated fatty alcohols and the like. These materials may be used singly or in combination of two or more of them.

Examples of the foaming agent include sodium lauryl sulfate, sodium lauroyl sarcosinate, sodium alkylsulfo succinate, coconut oil fatty acid monoglycerin sodium slufonate, α-olefin sodium slufonate, an N-acylamino acid salt such as N-acyl glutamate, 2-alkyl-N-carboxymethyl-N-hydroxyethyl imidazolinium betaine, maltitol fatty acid ester, sucrose fatty acid ester, a polyglyceryl fatty acid ester, fatty acid diethanolamide, polyoxyethylene sorbitan monostearate, polyoxyethylene hydrogenated castor oil, polyoxyethylene fatty acid ester, and the like. These materials may be used singly or in combination of two or more of them.

Examples of the lubricant include magnesium stearate, sucrose fatty acid ester, talc, hydrogenated oil and the like. These materials may be used singly or in combination of two or more of them.

Examples of the oil include coconut oil, olive oil, sesame oil, peanut oil, parsley oil, parsley seed oil, safflower oil and the like. These materials may be used singly or in combination of two or more of them.

Examples of the surfactant include sodium lauryl sulfate, α-olefin sodium slufonate, sodium dodecylbenzene sulfonate, sodium lauryl solfoacetate, sodium N-lauroyl sarcosinate, N-acylglutamate, sucrose fatty acid ester, polyoxyethyele hydrogenated castor oil, a polyoxyethylene polyoxypropylene block copolymer, alkyl glycosides, sorbitan fatty acid ester, polyoxyethylene sorbitan fatty acid ester, alkyldimethyl amine oxide, lauryl ethanol amide, sodium cocoyl sarcosinate, sodium N-lauroyl methyl taurine liquid and the like. These materials may be used singly or in combination of two or more of them.

Examples of the coloring agent include: a pigment such as Blue No. 1 and the like; a colorant such as titanium dioxide and the like; various kinds of dyes; and the like. These materials may be used singly or in combination of two or more of them.

Examples of the antioxidizing agent include dibutylhydroxyl toluene, butylhydroxyl anisole, erythorbic acid, propyl gallate, octyl gallate, d-δ-tocopherol, vitamin C, vitamin E, edetate disodium, calcium gluconate, and the like.

Examples of the chelate agent include edentates and the like.

Examples of the flavoring substance include camellia sinensis leaf extract, camellia sinensis leaf tar, sodium glutamate and the like. These materials may be used singly or in combination of two or more of them.

Examples of the moisturizing agent include amino acid or a salt thereof, pyrrolidone carboxylic acid, mucin, hyaluronic acid or a salt thereof, mucopolysaccharides such as chondroitin sulfate, sodium lactate, urea, panthenol, a natural extract constituent such as aloe extract, rosemary extract, thyme extract, camellia sinensis leaf extract (camellia sinensis leaf tar extract) and the like, as it is called, an extracellular matrix such as collargen and elastin and the like. These materials may be used singly or in combination of two or more of them.

Examples of the antibacterial agent include: a phenol based antibacterial agent such as isopropyl methyl phenol, triclosan, hinokitiol, thymol and the like; cetylpyridinium chloride, benzalkonium chloride, benzethonium chloride, dequalinium chloride, chlorhexidine hydrocholoride, chlorhexidine sodium gluconate, bisaabolol chlorhexidine, lactoferrin, paraben, butyl paraben, and the like. These materials may be used singly or in combination of two or more of them.

Examples of the anti-inflammatory drug include lysozyme chloride, ε-aminocaproic acid, aluminum hydroxyl allantoin, glycyrrhetic acid, glycyrrhizinates, guaiazulene sulphonic acid, acetic acid dl-α-tocopherol and the like. These materials may be used singly or in combination of two or more of them.

Examples of the fluoride include sodium fluoride, potassium fluoride, sodium monofluorophosphate, stannous fluoride and the like. These materials may be used singly or in combination of two or more of them.

Examples of the vitamin preparation include: vitamin A such as retinoic acid, β-carotene and the like; vitamin B such as pantothenic acid and salts thereof, niacin, biotin and the like; vitamin C such as ascorbic acid or salts thereof and derivatives thereof and the like; vitamin E such as α-tocopherol and the like; folic acid and the like. These materials may be used singly or in combination of two or more of them.

Examples of the crude drugs other than the crude drugs described above include german chamomile, Japanese valerian, jujube, hop, lavender, linden, pseudocydonia sinensis, lonicera japonical, sasa veitchii, elaeagnus, clove, panax notoginseng, salvia, soapberry, cinnamon bark, poria sclerotium, paony root, crataegus fruit, Japanese angelica root, theae folium, quercus saslicina, phellodendron bark, betula platyphylla, ginseng, gambier, turmeric, rosemary, and the like. These may be used singly or in combination of two or more of them.

In the case where the oral composition contain the crude drugs as described above, the oral composition may contain the crude drugs as described above, for example, in a state of having ground plants in the dry state. Further, the oral composition may contain them as the extract essence extracted by using the extract solvent such as water and the organic solvent or the extract medium such as the supercritical fluid, or the constituent (extract) obtained by removing the extract medium from the extract essence.

A configuration of the oral composition is not limited particularly. Examples of such a configuration include a liquid (emulsified form, solubilization form), a liquid form, a gel form, a paste form, a tablet form, a foam form, a powder form, a granular form and the like.

Examples of applications for the oral composition include: a dentifrice such as a toothpaste, a toothpowder, a liquid-like toothpaste, a tooth liquid and the like; a lozenge; a tablet (which includes a foaming tablet and the like); a cream agent; an ointment; an adhesive skin patch; a oral wetting agent; a mouth rinse; a mouth freshener; a tablet for gargle; a denture adhesive; a denture cleaner; a chewing gum; and the like.

<<Method for Producing Oral Composition>>

The oral composition of the present invention is able to be obtained by mixing each constituent as described above.

Especially, in the case where the oral composition contains the porous body, it is preferred that the crude drugs as described above are mixed with the porous body in advance, and then it is mixed with other constituents.

This makes it possible to reliably support the crude drugs in the pores of the porous body.

The preferred embodiments of the present invention have been described. However, the present invention is not limited thereto.

EXAMPLES

Hereinafter, description of the invention will be made on Examples and Comparative Examples in detail. However, the present invention is not limited thereto.

<<1>> Production of Liquid Composition

A liquid composition in each of the Examples and Comparative Examples was produced as follows.

Example 1

A liquid composition was obtained by dissolving only predetermined amounts (see Table 1) of freeze-dried powder of *Scutellaria* root extract liquid-J (produced by MARUZEN PHARMACEUTICALS CO., LTD.) as the extract of the *Scutellaria* root and *Platycodon* root dried essence-S (produced by Alps Pharmaceutical Ind. Co., Ltd.) as the extract of the *Platycodon* root with water.

Example 2

A liquid composition was obtained by dissolving only predetermined amounts (see Table 1) of freeze-dried powder of *Scutellaria* root extract liquid-J (produced by MARUZEN PHARMACEUTICALS CO., LTD.) as the extract of the *Scutellaria* root, *Platycodon* root dried essence-S (produced by Alps Pharmaceutical Ind. Co., Ltd.) as the extract of the *Platycodon* root, and *Rehmannia* root extract liquid-J (produced by MARUZEN PHARMACEUTICALS CO., LTD.) as the extract of the *Rehmannia* root with water.

Examples 3 to 11

Liquid compositions were produced in the same manner as the Example 2, except that a content ratio of each constituent of raw materials was changed as shown in Table 1.

Comparative Example 1

A liquid composition was produced in the same manner as the Example 1, except that the *Platycodon* root was not used as the raw material.

Comparative Example 2

A liquid composition was produced in the same manner as the Example 1, except that the *Scutellaria* root was not used as the raw material.

Comparative Example 3

A liquid composition was produced in the same manner as the Example 1, except that the *Scutellaria* root and the *Platycodon* root were not used as the raw material. In other words, the liquid composition of this Comparative Example is water.

Comparative Example 4

A liquid composition was produced in the same manner as the Example 2, except that the *Platycodon* root was not used as the raw material.

Comparative Example 5

A liquid composition was produced in the same manner as the Example 2, except that the *Scutellaria* root was not used as the raw material.

Comparative Example 6

A liquid composition was produced in the same manner as the Example 2, except that the *Scutellaria* root and the *Platycodon* root were not used as the raw material.

Table 1 shows compositions and the like of the liquid compositions obtained in the Examples and the Comparative Examples described above together. In Table 1, the content ratio of the *Scutellaria* root in the liquid composition was shown as $X_A$ (mass %), the content ratio of the *Platycodon* root in the liquid composition was shown as $X_B$ (mass %), and the content ratio of the *Rehmannia* root in the liquid composition was shown as $X_C$ (mass %).

TABLE 1

| | Content ratio[mass %] | | | | | | |
|---|---|---|---|---|---|---|---|
| | Scutel-laria root | Platy-codon root | Rehmannia root | Water | $X_B/X_A$ | $X_C/X_A$ | $X_C/X_B$ |
| Ex. 1 | 0.02 | 0.1 | — | Residue | 5 | 0 | 0 |
| Ex. 2 | 0.02 | 0.1 | 0.8 | Residue | 5 | 40 | 8 |
| Ex. 3 | 0.01 | 0.1 | 0.8 | Residue | 10 | 80 | 8 |
| Ex. 4 | 0.10 | 0.1 | 0.8 | Residue | 1 | 8 | 8 |
| Ex. 5 | 0.02 | 0.05 | 0.8 | Residue | 2.5 | 40 | 16 |
| Ex. 6 | 0.02 | 1.0 | 0.8 | Residue | 50 | 40 | 0.8 |
| Ex. 7 | 0.02 | 0.1 | 0.4 | Residue | 5 | 20 | 4 |
| Ex. 8 | 0.02 | 0.1 | 1.2 | Residue | 5 | 60 | 12 |
| Ex. 9 | 1.0 | 0.1 | 0.8 | Residue | 0.1 | 0.8 | 8 |
| Ex. 10 | 0.02 | 4.0 | 0.8 | Residue | 200 | 40 | 0.2 |
| Ex. 11 | 0.02 | 0.1 | 4.0 | Residue | 5 | 200 | 40 |
| Com. Ex. 1 | 0.02 | — | — | Residue | 0 | 0 | — |
| Com. Ex. 2 | — | 0.1 | — | Residue | — | — | 0 |
| Com. Ex. 3 | — | — | — | Residue | — | — | — |
| Com. Ex. 4 | 0.02 | — | 0.8 | Residue | 0 | 40 | — |
| Com. Ex. 5 | — | 0.1 | 0.8 | Residue | — | — | 8 |
| Com. Ex. 6 | — | — | 0.8 | Residue | — | — | — |

<<2>> Evaluations

The following evaluations were made by using the liquid compositions of the Examples and the Comparative Examples.

<<2-1>> Examination of suppressing Formation of Biofilm

*Porphyromonas gingivalis* (*Porphyromonas gingivalis* JCM12257) was prior-cultured at 37° C. for 24 hours in GAM medium (produced by Wako pure chemical Industries, Ltd.) to obtain a prior culture liquid.

The obtained prior culture liquid was added to a medium including Hemin-Menadione so that the number of bacterium became $10^7$ CFU/mL. Thus, a culture liquid was obtained. Thereafter, the culture liquid was disseminated to a 48 well plate every 0.5 mL.

0.5 mL of the liquid composition was added to the 48 well plate, and then it was anaerobically cultured at 37° for 24 hours.

After 24 hours, the 48 well plate was washed by a phosphate buffered saline (PBS) in two times, which had been prepared according to an usage using PBS(−) powder (produced by NISSUI PHARMACEUTICAL CO., LTD.). Thus, floating bacteria were removed.

0.1 mass % crystal violet solution (produced by Wako pure chemical Industries, Ltd.) was added to it, so that the formed biofilm was stained.

Thereafter, the biofilm was washed by PBS, and then the crystal violet was extracted by ethanol. Next, an amount of the biofilm was determined quantity by an absorption spectrometer to evaluate according to the following criteria. The lower the absorbance is, the lower the amount of the biofilm is, so that it is possible to suppress the plaque to cause the periodontal disease from being formed.

A: An absorbance is lower than 1.0.
B: An absorbance is 1.0 or more but lower than 5.5.
C: An absorbance is 5.5 or more but lower than 7.0.
D: An absorbance is 7.0 or more but lower than 9.5.
E: An absorbance is 9.5 or more.

<<Color Tone>>

In the liquid composition of each of the Examples and the Comparative Examples, the absorbance of light having a wavelength of 286 nm was measured to evaluate according to the following criteria. If the absorbance is high, an appearance of the liquid composition is inferior. If the absorbance is low, the appearance thereof is excellent.

A: An absorbance is lower than 25.0.
B: An absorbance is 25.0 or more.

These results are shown in Table 2. Further, the concentration (content ratio) of each constituent at the time of the above examination is shown together in Table 2.

TABLE 2

| | Content ratio at the time of examination (mass %) | | | | Examination of suppressing formation of biofilm (plaque to cause periodontal disease) | Color tone |
|---|---|---|---|---|---|---|
| | Scutel-laria root | Platy-codon root | Rehman-nia root | Water | | |
| Ex. 1 | 0.01 | 0.05 | — | Residue | C | A |
| Ex. 2 | 0.01 | 0.05 | 0.4 | Residue | A | A |
| Ex. 3 | 0.005 | 0.05 | 0.4 | Residue | B | A |
| Ex. 4 | 0.05 | 0.05 | 0.4 | Residue | A | A |
| Ex. 5 | 0.01 | 0.025 | 0.4 | Residue | B | A |
| Ex. 6 | 0.01 | 0.5 | 0.4 | Residue | A | A |
| Ex. 7 | 0.01 | 0.05 | 0.2 | Residue | B | A |
| Ex. 8 | 0.01 | 0.05 | 0.6 | Residue | A | A |
| Ex. 9 | 0.5 | 0.05 | 0.4 | Residue | A | B |
| Ex. 10 | 0.01 | 2.0 | 0.4 | Residue | A | B |
| Ex. 11 | 0.01 | 0.05 | 2.0 | Residue | A | B |
| Com. Ex. 1 | 0.01 | — | — | Residue | E | A |
| Com. Ex. 2 | — | 0.05 | — | Residue | E | A |
| Com. Ex. 3 | — | — | — | Residue | E | A |
| Com. Ex. 4 | 0.01 | — | 0.4 | Residue | E | A |
| Com. Ex. 5 | — | 0.05 | 0.4 | Residue | E | A |
| Com. Ex. 6 | — | — | 0.4 | Residue | E | A |

As shown from Table 2 clearly, the excellent effects were obtained in the present invention. In contrast, the sufficient results could not be obtained in the Comparative Examples. Specifically, as shown in the Example 1 and the Comparative Examples 1 and 2 of Table 2 clearly, even if there is no effect in the concentration of each of the *Scutellaria* root and the *Platycodon* root by itself, the remarkable effects were obtained by using them together. Further, as shown in the Example 2 and the Comparative Examples 4 and 5 clearly, even if there is no effect in the concentrations of two constituents as the *Scutellaria* root and the *Rehmannia* root, and the *Platycodon* root and the *Rehmannia* root, the remarkable effects were obtained by mixing the three constituents together.

As described later, a toothpaste as the oral composition was produced by using the liquid composition of the Example 2. Thereafter, the evaluations for sense of use were carried out.

<Prescription A>

First, the liquid composition of the Example 2 was added to zeolite as the porous body having a predetermined amount.

Next, this mixture was dried, and then the extracts of the crude drugs were supported in the pores of the porous body.

Then, the toothpaste as the liquid composition was produced by the ordinary method in accordance with the following prescription (unit: mass %).

| | |
|---|---|
| Scutellaria root | 0.01 |
| Platycodon root | 0.05 |
| Rehmannia root | 0.4 |
| Calcium carbonate | 30.0 |
| Silicic acid anhydride | 5.0 |
| Zeolite | 5.0 |
| Sorbit liquid | 15.0 |
| Concentrated glycerin | 10.0 |
| Carboxymethylcellulose sodium | 1.0 |
| Sodium lauryl sulfate | 0.5 |
| Saccharin sodium | 0.05 |
| Flavor | 1.0 |
| Water | Residue |

<Prescription B>

First, the liquid composition of the Example 2 was mixed with each constituent of the following mass %. Then, the toothpaste as the liquid composition was produced by the ordinary method in accordance with the following prescription (unit: mass %).

| | |
|---|---|
| Scutellaria root | 0.01 |
| Platycodon root | 0.05 |
| Rehmannia root | 0.4 |
| Calcium carbonate | 30.0 |
| Silicic acid anhydride | 5.0 |
| Sorbit liquid | 15.0 |
| Concentrated glycerin | 10.0 |
| Carboxymethylcellulose sodium | 1.0 |
| Sodium lauryl sulfate | 0.5 |
| Saccharin sodium | 0.05 |
| Flavor | 1.0 |
| Water | Residue |

The toothpaste of the prescription B is different from the toothpaste of the prescription A in that it does not contain zeolite as the porous body and the content ratio of the water become high in the amount of zeolite.

15 adults put a predetermined amount (about 1 g) of each of the two kinds of obtained toothpastes (oral composition) as described above on a commercially available toothbrush to use it. The 15 adults evaluated the sense of use at that time.

As a result, all of 15 adults answered that the toothpaste of the prescription A (oral composition) was less than the toothpaste of the prescription B (oral composition) at the time of using them in the uncomfortable feeling such as bitter felling.

By using the liquid composition (composition containing water) of each of the Examples and the Comparative Examples, a mouth rinse (mouthwash), a denture cleaner and a denture adhesive as the oral composition were produced by the ordinary method in accordance with the following prescription (unit: mass %).

<Mouth Rinse>

| | |
|---|---|
| Scutellaria root | 0.01 |
| Platycodon root | 0.05 |
| Rehmannia root | 0.4 |
| Denatured alcohol No. 56 | 5.0 |
| Polyoxyethylene hydrogenated castor oil | 0.5 |
| Concentrated glycerin | 5.0 |
| Xylitol | 5.0 |
| Cetylpyridinium chloride | 0.05 |
| Dipotassium glycyrrhizinate | 0.05 |
| Eethyl para-hydroxybenzoate | 0.05 |
| Propyl para-hydroxybenzoate | 0.05 |
| Citric acid | 0.03 |
| Sodium citrate | 0.12 |
| Flavor | 1.0 |
| Water | Residue |

<Denture Cleaner>

| | |
|---|---|
| Scutellaria root | 0.01 |
| Platycodon root | 0.05 |
| Rehmannia root | 0.4 |
| Silicic acid anhydride | 3.0 |
| Hydrous silicic acid | 10.0 |
| Polyethylene glycol 400 | 5.0 |
| Concentrated glycerin | 35.0 |
| 60 mass % sorbit liquid | 30.0 |
| Sodium lauryl sulfate | 2.0 |
| Carboxymethylcellulose sodium | 1.5 |
| Flovor | 1.0 |
| Sodium carbonate | Moderate amount |
| Water | Residue |

<Denture Adhesive>

| | |
|---|---|
| Scutellaria root | 0.01 |
| Platycodon root | 0.05 |
| Rehmannia root | 0.4 |
| Zeolite | 5.0 |
| Concentrated glycerin | 30.0 |
| Carboxymethylcellulose sodium | 3.0 |
| Polyoxyethylene hydrogenated castor oil | 1.0 |
| Cetylpyridinium chloride | 0.05 |
| Flavor | 1.0 |
| Sodium carbonate | Moderate amount |
| Water | Residue |

These were evaluated in the same manner described above, so that the same effects as described above were obtained.

INDUSTRIAL APPLICABILITY

The present invention characterize in that the oral composition contains the *Scutellaria* root and the *Platycodon* root. Therefore, the oral composition of the present invention has the forming suppression effect of the plaque to cause the periodontal disease. The effect is obtained in a lower dosage than a use dosage of a single crude drug. Accordingly, the oral composition of the present invention has industrial applicability.

What is claimed is:

1. A dentifrice comprising *Scutellaria* root, *Rehmannia* root, and *Platycodon* root,
   wherein a content ratio of the *Scutellaria* root in the dentifrice is 0.0001 mass % or more and 2 mass % or less, a content ratio of the *Platycodon* root in the dentifrice is 0.0001 mass % or more and 2 mass % or less, and a content ratio of the *Rehmannia* root in the dentifrice is 0.001 mass % or more and 2 mass % or less.

2. The dentifrice as claimed in claim 1, wherein when the mass % of the *Scutellaria* root in the dentifrice is defined as $X_A$ and the mass % of the *Rehmannia* root in the dentifrice is defined as $X_C$, the following relation is satisfied: $4 \leq X_C/X_A \leq 120$.

3. The dentifrice as claimed in claim 1, wherein when the mass % of the *Platycodon* root in the dentifrice is defined as $X_B$ and the mass % of the *Rehmannia* root in the dentifrice is defined as $X_C$, the following relation is satisfied: $0.0005 \leq X_C/X_B \leq 20000$.

4. The dentifrice as claimed in claim 1, wherein the content ratio of the *Scutellaria* root in the dentifrice is 0.0005 mass % or more and 0.5 mass % or less and the content ratio of the *Platycodon* root in the dentifrice is 0.001 mass % or more and 1 mass % or less.

5. The dentifrice as claimed in claim 1, wherein the content ratio of the *Rehmannia* root in the dentifrice is larger than the content ratio of the *Scutellaria* root in the dentifrice.

* * * * *